US006514394B1

(12) United States Patent
Vangrunderbeek et al.

(10) Patent No.: US 6,514,394 B1
(45) Date of Patent: Feb. 4, 2003

(54) SENSOR FOR APPLICATION IN MOLTEN METALS

(75) Inventors: Johan Vangrunderbeek, Zemst (BE); Pieter Lens, Arendonk (BE); Jan Luyten, Vaalbeek (BE)

(73) Assignee: Vlaamse Instelling Voor Technologisch Onderzoek (V.I.T.O.), Mol (BE)

( * ) Notice: Subject to any disclaimer, the term of this patent is extended or adjusted under 35 U.S.C. 154(b) by 0 days.

(21) Appl. No.: 09/623,143

(22) PCT Filed: Feb. 26, 1999

(86) PCT No.: PCT/BE99/00030
§ 371 (c)(1),
(2), (4) Date: Oct. 25, 2000

(87) PCT Pub. No.: WO99/45380
PCT Pub. Date: Sep. 10, 1999

(30) Foreign Application Priority Data

Mar. 6, 1998 (BE) .......................................... 09800180

(51) Int. Cl.⁷ .............................................. G01N 27/26
(52) U.S. Cl. ...................... 204/400; 204/422; 205/775; 205/790
(58) Field of Search .................. 204/400, 422, 204/423; 205/775, 783.5, 790

(56) References Cited

U.S. PATENT DOCUMENTS

| | | | | |
|---|---|---|---|---|
| 3,208,919 A | * | 9/1965 | Sennett et al. |
| 3,784,459 A | * | 1/1974 | Jackson |
| 3,980,543 A | * | 9/1976 | Eckfeldt |
| 4,098,651 A | * | 7/1978 | Alder |
| 4,657,641 A | * | 4/1987 | Nakamura et al. |
| 5,445,725 A | * | 8/1995 | Koide et al. |
| 6,083,368 A | * | 7/2000 | Abe et al. |

FOREIGN PATENT DOCUMENTS

| | | |
|---|---|---|
| DE | 195 30 910 | 2/1997 |
| EP | 0 493 878 | 7/1992 |
| JP | 56168152 | 12/1981 |

OTHER PUBLICATIONS

Vangrunderbeek et al., "Immobilised Molten Salt Membrane based Magnesium Sensor for Aluminum–Magnesium Melts," *Ionics*, 1 (1995), month unavailable, pp. 59–62.

Larose et al., "Solid electrolyte probes for magnesium, calcium and strontium in molten aluminum," *Solid State Ionics*, 47 (1991), month unavailable, pp. 287–295.

Zhang et al., "Electrochemical sensor for measuring magnesium content in molten aluminum," *Journal of Applied Electrochemistry*, 26 (1996), pp. 269–275.

International Search Report for application PCT/BE99/00030 dated May 4, 1999.

* cited by examiner

*Primary Examiner*—T. Tung
(74) *Attorney, Agent, or Firm*—Merchant & Gould P.C.

(57) ABSTRACT

An electrochemical sensor to measure the activity of a metallic component in a molten metal, comprising the molten metal as the measuring electrode, a reference electrode containing the metallic component to be measured, separated from each other by a liquid ion-conducting halide comprising the metallic component to be measured and immobilized in a non-conducting porous support fabricated from a material inert or almost inert to the molten metal, the halide and the reference electrode material, and whereby the reference electrode further comprises an external connection comprising an electric wire held in an electric isolating material which is chemically inert or almost inert to the molten metal and the reference electrode material, characterized in that the sealing of the reference electrode which is adapted to be sealed is done by a high temperature cement and by the molten metal itself and by a gas tight sealing of the external connection above the melt, and the reference electrode is introduced by a melt process.

23 Claims, 7 Drawing Sheets

SENSOR FOR APPLICATION IN MOLTEN METALS

FIELD OF THE INVENTION

This invention relates to an electrochemical immersion sensor for the determination of the concentration of a metallic component in a molten metal, comprising the molten metal as the measuring electrode and a reference electrode, the latter containing the metallic component to be measured, separated from each other by a liquid ion-conducting halide containing the metallic component to be measured and immobilised in a non-conducting porous support fabricated from a material which is inert or almost inert to the molten metal, the halide and the reference electrode material, wherein the sealing of the reference electrode is at least partly provided by the molten metal itself and wherein the reference electrode is introduced by a melt process. This invention further relates to a method for producing said sensor. The term "molten metal" as used herein is understood to mean the melt of a metal or alloy.

STATE OF THE ART

An electrochemical sensor, in particular able to measure the aluminium concentration in a molten metal, is known from patent application EP 0 493 878 A2. The sensor comprises a gas tight holder fabricated of quartz or pyrex with a projection attached to the tip, which is removable by snapping in use to allow the enclosed ion-conducting material or electrolyte to contact the molten metal. NaCl—AlCl$_3$ electrolyte is used as the ion-conducting material whereby the NaCl acts as saturated solid component. A pure aluminium wire immersed in the ion-conducting material is used as the reference electrode, whereas the molten metal itself serves as the measuring electrode. In a particular embodiment of the invention, a dense β-alumina membrane immersed in the ion-conducting material separates the reference and measuring electrodes. If the composition of the electrolyte remains constant, the aluminium activity at the reference electrode is fixed and known, and if the aluminium activity at the measuring electrode in the molten metal is established, the sodium activity at both sides of the membrane will be known and the value of the aluminium activity at the measuring side can be determined by the following equilibrium: 3 Na+AlCl$_3$=3 NaCl+Al. A sodium concentration cell is obtained. By measuring the EMF of this sodium concentration cell, the aluminium activity or concentration in the molten metal can be deduced from Nernst's equation.

Most important disadvantage of said sensor is its fragility (the salt can easily be lost), due to which said sensor can not be used in agitated molten metals. Another disadvantage of said sensor is the stringent requirements to the composition of the electrolyte. Another disadvantage is the indirect determination of the aluminium concentration via a sodium concentration cell. It's further disadvantageous that said sensor can not be used in liquid aluminium since most of the aluminium alloys contain sodium disturbing the above mentioned sodium equilibrium. User practice has further indicated that said sensor should be sufficiently immersed in the molten metal (at least 20 cm).

Other publications are "Immobilised Molten Salt Membrane based Magnesium Sensor for Aluminium-Magnesium Melts", Vangrunderbeek et al., Ionics 1 (1995) p. 59–62, and "Electrochemical Sensor for Measuring Magnesium Content in Molten Aluminium", Zhang et al., Journal of Applied Electrochemistry, 26 (1996), 269–275. These documents describe sensors for measuring the Mg activity in Al—Mg melts. Disadvantage of said sensors is the insufficient sealing of said sensors with cements for use in an industrial process.

AIMS OF THE INVENTION

This invention is aimed to provide a new electrochemical sensor for continuously measuring of the concentration of a metallic component in a molten metal in an industrial environment. Another aim of this invention is to provide a method to produce such a sensor.

GENERAL DESCRIPTION OF THE INVENTION

The first embodiment of this invention is an electrochemical sensor to measure the activity of a metallic component in a molten metal, comprising the molten metal as the measuring electrode and a reference electrode, the latter comprising the metallic component to be measured, separated from each other by a liquid ion-conducting halide comprising the metallic component to be measured and immobilized in a non-conducting porous support fabricated from a material substantially inert to the molten metal, the halide and the reference electrode material, and whereby the reference electrode further comprises an external connection comprising electrically conducting wire immersed in an electric isolating material which is chemically substantially inert to the molten metal and the reference electrode material, characterized in that the sealing of the reference electrode is provided by a high temperature cement and the molten metal itself and by a gas tight sealing of the external connection above the melt, and by melting the reference material inside the electrochemical sensor. The porous support is preferably shaped as one closed end tube.

The liquid ion-conducting halide preferably contains chlorides, fluorides and/or bromides, of which at least one comprises the metallic component to be measured.

The porous support preferably has porosity between 20 and 50%, most likely between 30 and 40%. As porosity is higher the strength of the porous support will be lower, leading to a limited applicability in an industrial process. When porosity is too low, the conductivity of the impregnated halide will be negatively influenced resulting in an increase of the reaction time of the sensor upon immersion in the molten metal and in a decrease of the obtained accuracy. When the porosity and the pore size are measured by a Coulter Porometer® and Coulter Porofil™ wetting agent, a minimal test gas flow (pressurized air) of 50% should be measured for the pores between 0.5 and 5 μm, most likely between 0.5 and 1.5 μm. The pores are open pores permitting ionic transport. When the average pore size is lower, the ion conductivity of the halide is too low to obtain useful measurements. When the average pore size is higher, the impregnated halide can leave the porous support more easily and the molten metal can penetrated the porous support, making the sensor unclear.

In another embodiment, the porous support is manufactured of MgO. The MgO powder used to fabricate the porous support preferably has a purity of at least 99.5%.

In another embodiment of this invention, the porous support has been obtained by compacting and subsequent sintering of a MgO powder with a grain size distribution of at least 200 mesh or a largest grain size of 74 micrometer.

For the determination of Mg in an melt of an Al alloy, the ceramic tube used to protect the electrically conducting wire for the external connection of the reference electrode, is preferably not made of SiO$_2$ containing material, since $SiO_2$ reacts with the Mg used in the reference. The electric contact with the reference electrode is obtained by connecting the pure Mg with a suitable electrically conducting wire, preferably Mo, Ta or W. The electric contact with the measuring electrode can be very easily obtained via an electrically conducting wire in the molten metal, preferably made of the same material as the electrically conducting wire of the reference electrode.

In a further embodiment, the above-described embodiment is contained in a holder made of a material, which is substantially insoluble in the molten metal.

Said holder can be characterized in that it is provided with a ceramic or refractory material in the vicinity of the metal surface. In a preferred embodiment, said holder is made of a functional conducting material so that said holder serves at the same time as an electric connection for the measuring electrode of the electrochemical sensor. The holder can contain a thermocouple as well.

A second main embodiment of this invention is a method to fabricate an electrochemical sensor to measure the activity of a metallic component in a molten metal, comprising the melt as the measuring electrode, a reference electrode, the latter comprising the metallic component to be measured, separated from each other by a liquid ion-conducting halide comprising the metallic component to be measured and immobilized in a non-conducting porous support fabricated from a material substantially inert to the molten metal, the halide and the reference electrode material and wherein the reference electrode contains an external connection consisting of an electrically conducting wire in an electric isolating protection material, chemically substantially inert, characterised in that the method is built up according to the following sequential steps:

sealing of the porous support containing the reference electrode material and the external connection, using a high temperature cement, immobilizing the halide into the porous support at a temperature above the melting temperature of the reference electrode material or melting of the electrode material followed by immobilizing the halide into the porous support at a temperature lower than the melting temperature of the reference electrode material so that in both cases the reference electrode material is introduced by melting the reference material inside the electrochemical sensor, sealing of the external connection of the reference electrode above the melt using a gas tight paste, and in-situ completion of the sealing of the sensor by totally immersing the porous support of the sensor under the melt surface.

A further characteristic of this invention is the use of the sensor as described above or manufactured according to the method as described above for measuring the activity of a metallic component in a molten metal.

DETAILED DESCRIPTION OF THE INVENTION

The electrochemical sensor according to this invention is in particular able to continuously measure during several hours the concentration of a metallic component in a molten metal. For example, the sensor can be immersed in a molten metal in the runner as well as in the foundry furnace or any other melt, even inductively heated. Due to the short reaction time upon immersion, the sensor also can be used for single shot measurements, which last only for a couple of minutes.

By selecting suitable components, the sensor of this invention can be introduced for continuously measuring of the concentration of different metallic components in a variety of molten metals.

This invention will now be described by a number of examples and drawings that are non-limiting to the scope of this invention.

EXAMPLE 1

Figure 1:
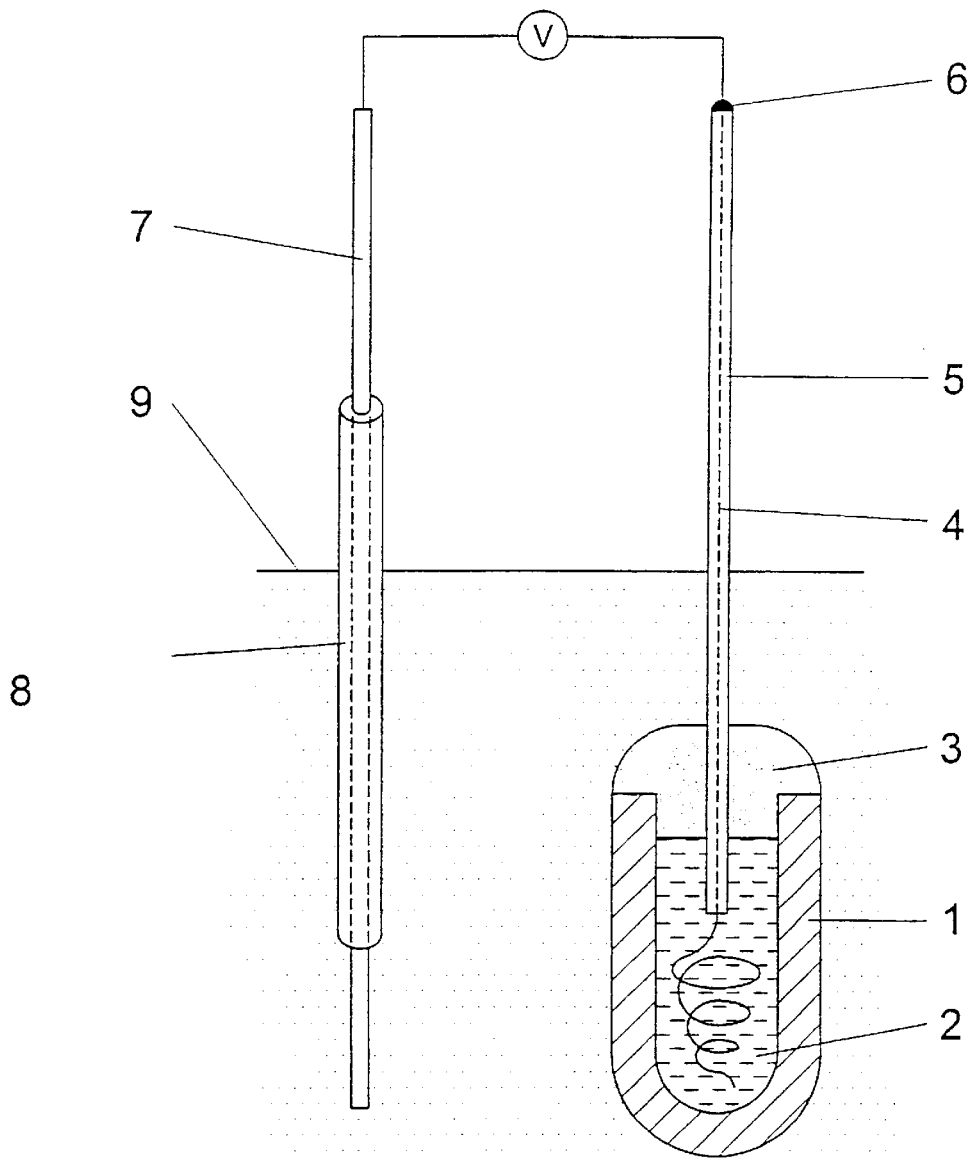
FIG. 1 describes a sensor according to this invention wherein the sensor is completely immersed in the molten metal.

FIG. 1 schematically describes the sensor according to the invention being completely immersed in the molten metal. In FIG. 1, (1) is the porous support impregnated with a halide, (2) the reference electrode, (3) a high temperature cement, preferably zirconia based, to seal the porous support, (4) an electric wire for the reference electrode, (5) a ceramic tube to protect the electric wire of the reference electrode, (6) vacuum paste for the ceramic tube preferably with a leak rate better than $10^{-6}$ mbar liter $sec^{-1}$, (7) an electric wire for the measuring electrode, (8) a tube made of a ceramic or refractory material, and (9) the surface of the molten metal.

Figure 2:
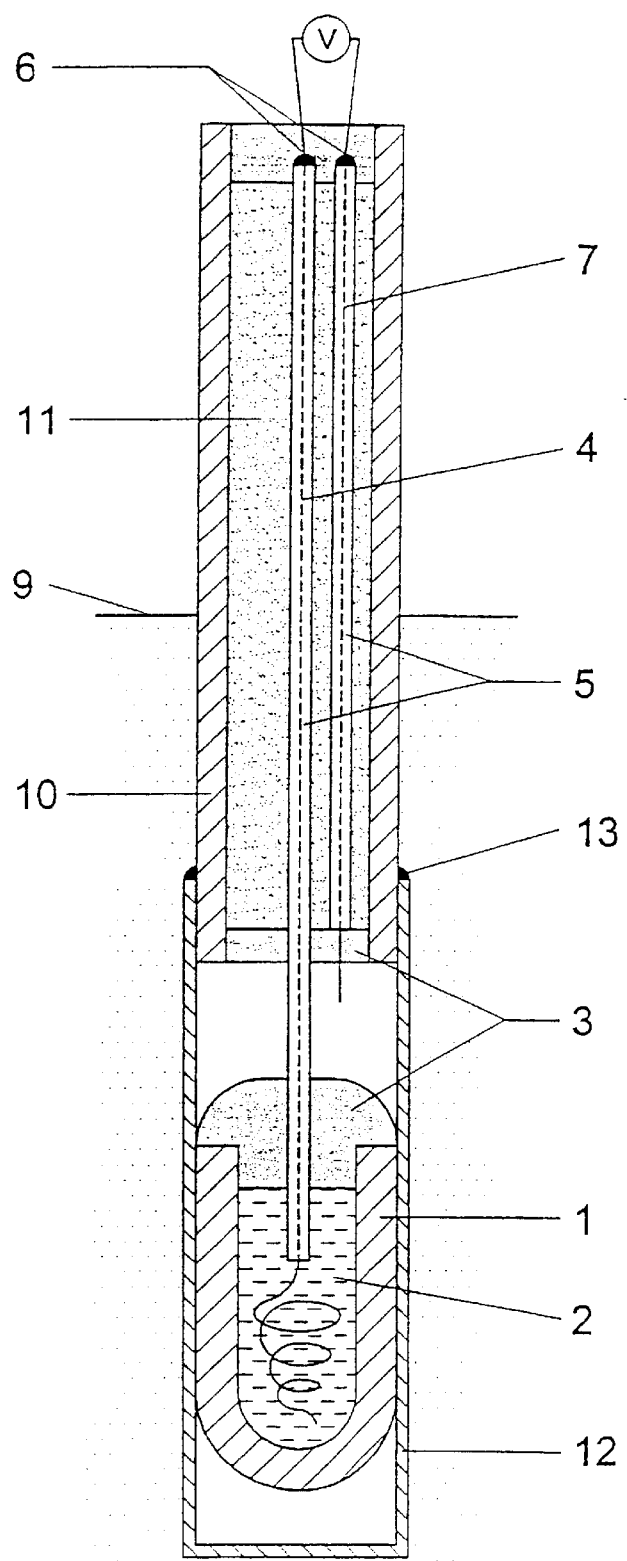
FIGS. 2 and 3 are other embodiments of the sensor according to this invention.

FIG. 2 schematically describes a further embodiment of the sensor according to the invention. In this embodiment, the sensor from FIG. 1 is contained in holder (10) made of a suitable material, e.g. steel, carbon, molybdenum, alumina, . . . The electric wire of the measuring electrode (7) is touching the molten metal at the bottom of the sensor holder (10), which is closed at the bottom with a high temperature cement (3). Further the sensor possibly contains a filler material (11) preferably a powder, and a fusible cap (12) which is connected to the holder (10) by means of a joint (13). When the sensor is immersed in the molten metal, the cap (12) will melt. The thermal shock of the sensor is herewith decreased. In FIG. 2 the cap is still present, but once in operation it will melt immediately after immersion in the molten metal, the porous support coming into contact with the molten metal as depicted schematically in FIG. 1.

Figure 3:
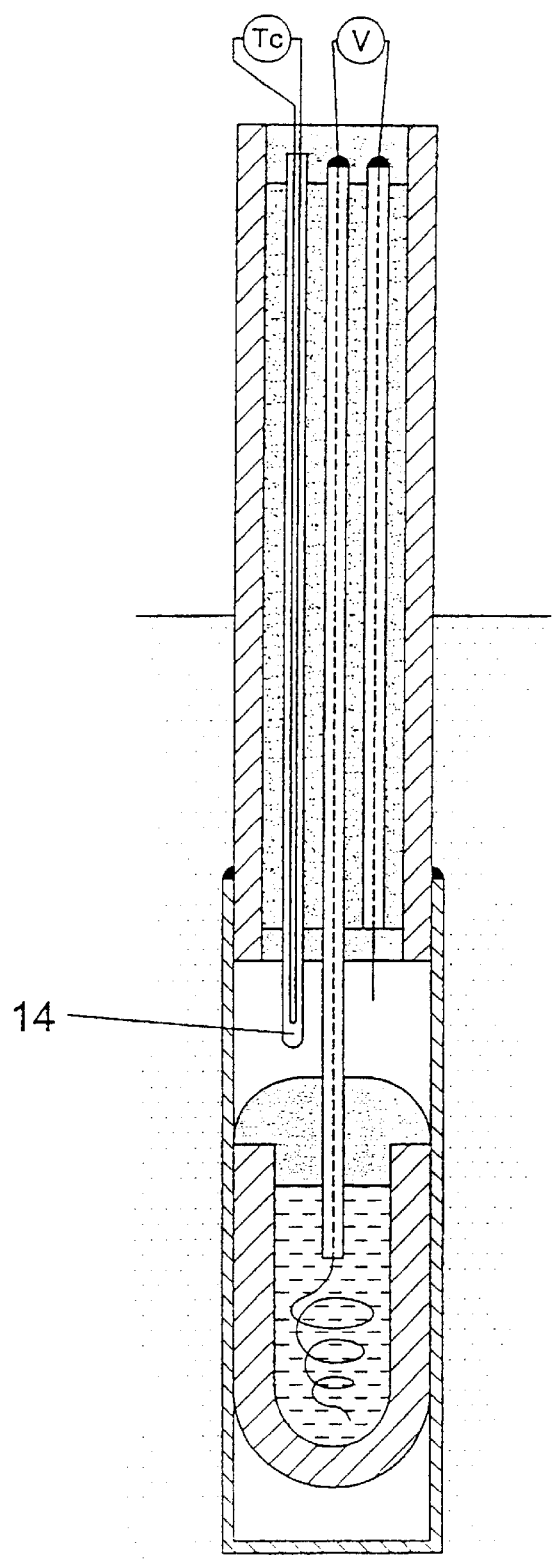

In FIG. 3 a further embodiment of the sensor from FIG. 2 is schematically given. In this embodiment, the sensor also contains a thermocouple (14), possibly enclosed in a ceramic tube, which is contained in the sensor holder (10) and contacts the molten metal. A compact and robust sensor is obtained with a short reaction time on immersion and which is applicable in an industrial environment.

Figure 4:
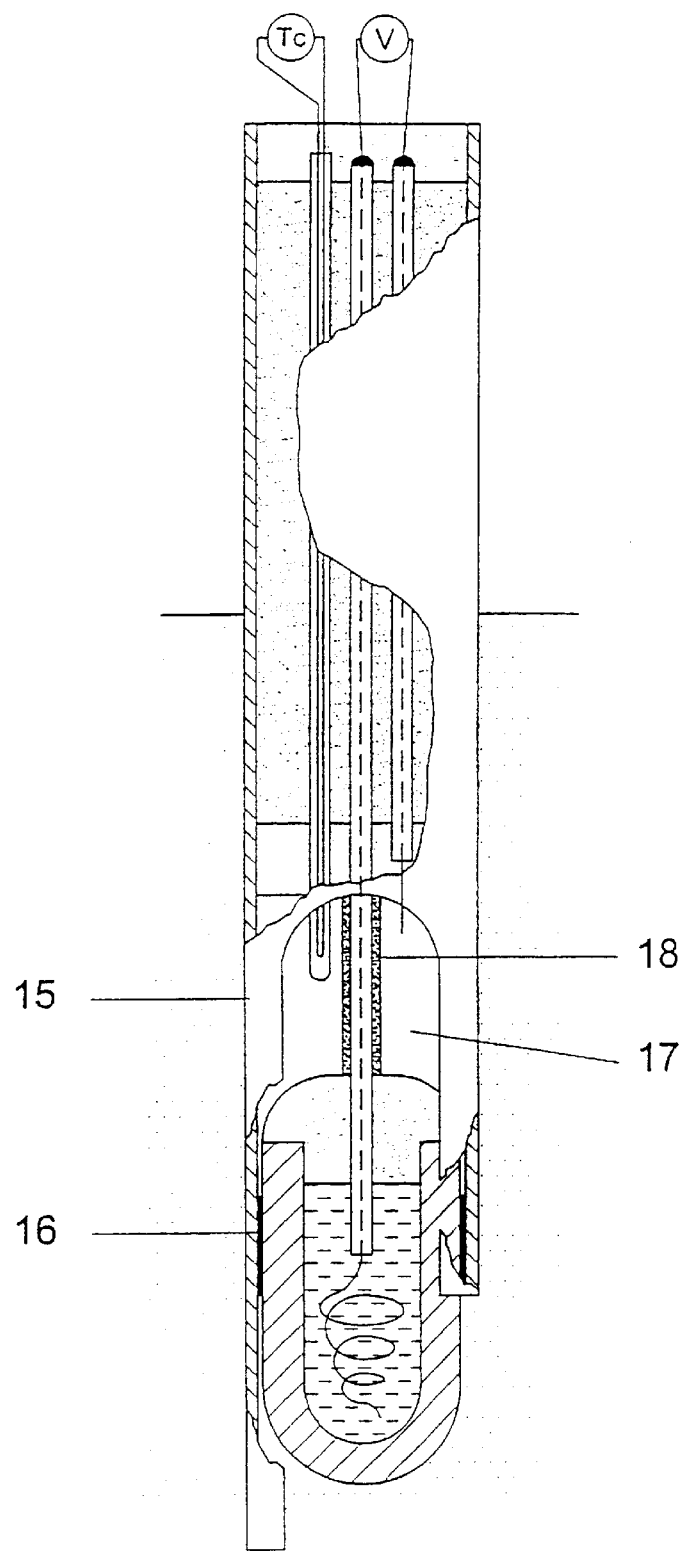
FIG. 4 is a particular embodiment of the sensor according to this invention.

In FIG. 4 a further embodiment of the sensor according to this invention is given. In this embodiment, the holder (10) is provided with one or more lips (15) that are at least as long as the porous support (1) and are possibly connected to the latter with a cement (16). The holder is further provided with slits (17) to permit the molten metal to flow above the porous support. Correct operation of the sensor implies that the surface of the molten metal (9) is at a higher level compared to the slits (17). The ceramic tube can be provided with a fusible foil or tube (18) in order to decrease the thermal shock of the ceramic tube upon immersion.

When the sensor according to this invention is used to measure the magnesium concentration in an aluminium melt, the halide preferably contains $MgCl_2$—KCl, the reference electrode preferably pure magnesium metal and the electric wires for reference and measuring electrode preferably Mo. If present, the cap and the foil or the tube around the ceramic tube of the reference electrode external connection are preferably made of aluminium. The sensor is based on the principle of an electrochemical concentration cell:

(+) Mo, Al—Mg (l)/$MgCl_2$—KCl/Mg (l), Mo (−).

The voltage or electromotive force (EMF) generated by this magnesium concentration cell is related to the magnesium activity or concentration (preferably in weight percent or wt %) by:

an industrial aluminium cast shop as a function of time. Temperature of the aluminium was 710° C. Three samples for spectrometer analysis were also taken as function of time. The results of the latter are given in FIG. 5 with error bars equal to two standard deviations (according to the overall sampling procedure for spectrometer analysis).

In this example, the sensor from example 1 is used, wherein the porous support is made of MgO, the halide contains $MgCl_2$, the reference electrode preferably consists of pure Mg, the electric wires of the electrodes preferably consist of Mo and the fusible cap and foil or tube preferably consist of aluminium.

Figure 5:
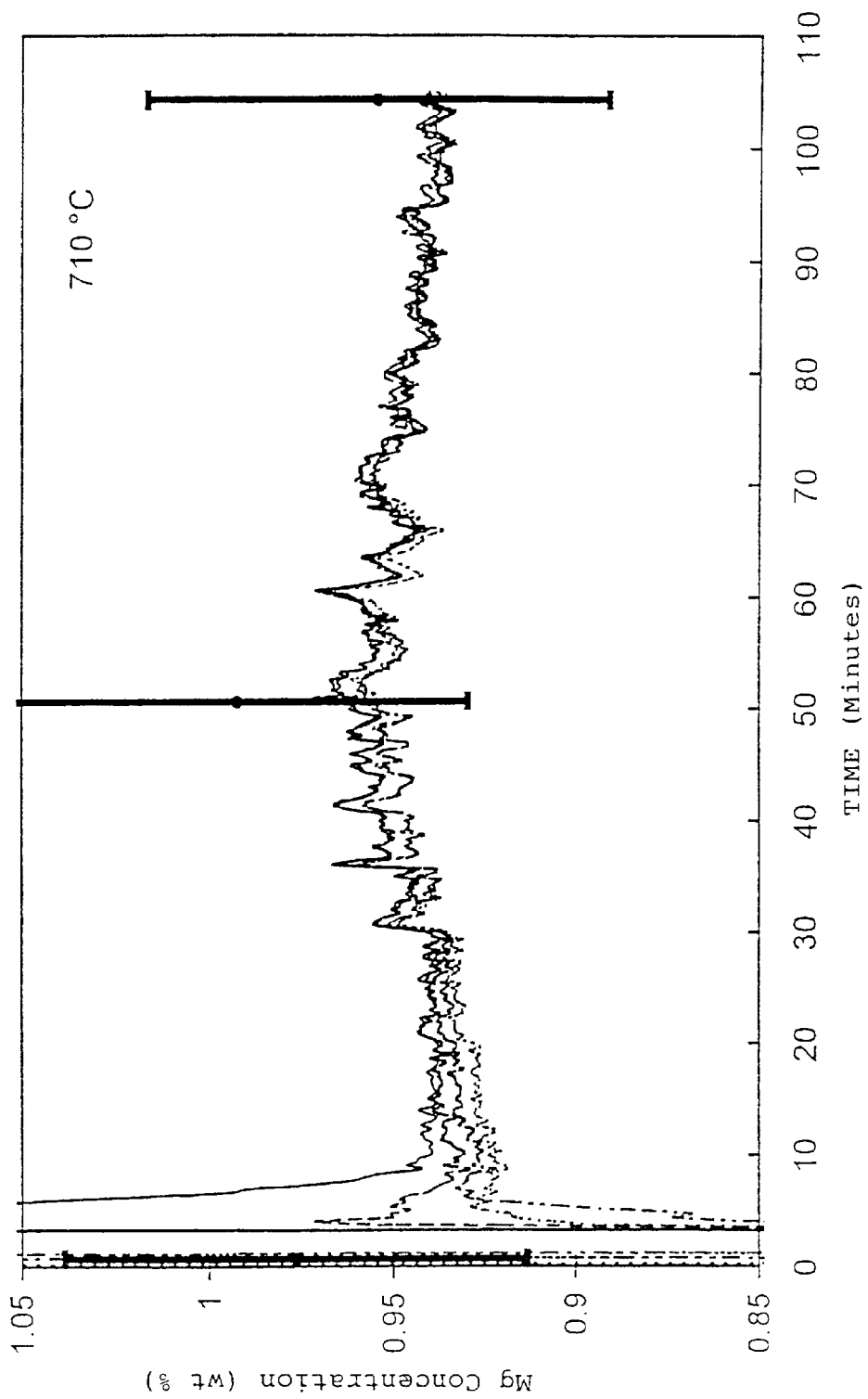
FIG. 5 gives the results of a measurement of the magnesium concentration in an aluminium melt in the runner as function of the measuring time.

From the results in FIG. 5 it can be deduced that the sensors according to this invention have a short stabilization time after immersion in the molten aluminium. The accuracy of the sensors is well between two standard deviations or the 95% confidence interval of the spectrometer analysis that is used for quality control. The sensors used are made by the method according to this invention wherein the porous support is made from MgO powder with 99.5% purity. The porous support obtained had porosity of 35% and pore size of 0.8 micrometer on the average, whereby 50% of the test gas flow, i.e. pressurized air,

TABLE 1

| Mg concentration Spectrometer (wt %) | Sensor 1 emf (V) | Sensor 2 emf (V) | Sensor 3 Emf (V) | Sensor 4 emf (V) | sensor 5 emf (V) | Sensor 6 emf (V) | Sensor 7 emf (V) | mean emf (V) | Standard Deviation (V) |
|---|---|---|---|---|---|---|---|---|---|
| .23 | .2544 | .2538 | .2539 | .254 | .2542 | .2534 | .2538 | .2539 | .0003 |
| .48 | .2251 | .2248 | .2247 | .2249 | .2251 | .2244 | .2247 | .2248 | .0002 |
| .73 | .2081 | .2079 | .2078 | .2081 | .2082 | .2076 | .2076 | .2079 | .0002 |
| .94 | .1963 | .1963 | .1961 | .1961 | .1964 | .1959 | .1959 | .1962 | .0002 |
| 1.19 | .1872 | .1873 | .1871 | .1871 | .1874 | .1868 | .1866 | .1871 | .0003 |
| 1.41 | .1797 | .1799 | .1795 | .1795 | .1798 | .1794 | .1791 | .1796 | .0003 |
| 1.62 | .1735 | .1738 | .1737 | .1731 | .1735 | .1732 | .1729 | .1734 | .0003 |
| 1.9 | .1681 | .1682 | .168 | .1674 | .1679 | .1677 | .1675 | .1679 | .0003 |
| 2.19 | .1619 | .162 | .1612 | .1616 | .1618 | .1614 | .1613 | .1616 | .0003 |
| 2.43 | .1576 | .1577 | .1569 | .1574 | .1574 | .1569 | .157 | .1573 | .0003 |
| 2.74 | .1538 | .1538 | .1527 | .1536 | .1535 | .1531 | .1533 | .1534 | .0004 |
| 3. | .1499 | .15 | .15 | .1497 | .1495 | .1495 | .1496 | .1497 | .0002 |
| 3.28 | .1466 | .1467 | .1463 | .1464 | .1461 | .1463 | .1464 | .1464 | .0002 |
| 3.57 | .1434 | .1435 | .143 | .1433 | .1428 | .1431 | .1432 | .1432 | .0002 |
| 3.77 | .1406 | .1407 | .1402 | .1406 | .14 | .1403 | .1404 | .1404 | .0002 |
| 4.03 | .138 | .1382 | .1374 | .1382 | .1375 | .1378 | .1379 | .1378 | .0003 |
| 4.3 | .1359 | .1359 | .1352 | .136 | .1356 | .1356 | .1357 | .1357 | .0003 |
| 4.6 | .1332 | .1334 | .1326 | .1334 | .1332 | .1331 | .133 | .1331 | .0003 |
| 4.88 | .1307 | .1308 | .1301 | .1308 | .1307 | .1306 | .1305 | .1306 | .0003 |
| 5.18 | .1287 | .1287 | .1279 | .1286 | .1288 | .1284 | .1285 | .1285 | .0002 |

$E/T = cst + cst' \ln (a_{(Mg\ in\ Al—Mg)}/a_{(Mg\ reference)}) = cst + cst' \ln (a_{(Mg\ in\ Al—Mg)}) = cst + cst' \ln (wt\ \%\ Mg\ in\ Al—Mg + cst'')$ wherein E: the EMF T: the temperature $a_{(Mg\ in\ Al—Mg)}$: magnesium activity in aluminium melt $a_{(Mg\ reference)}$: magnesium activity in the reference electrode and $a_{(Mg\ reference)} = 1$ for pure magnesium.

The cst" contains the activity coefficient of magnesium in aluminium. The three constants can be determined by a single and general calibration.

EXAMPLE 2

Four electrochemical sensors according to this invention are used to continuously measure the magnesium concentration in aluminium after the degassing unit in the runner of permeates the support. The grain size distribution of the MgO powders was 325 mesh. The halide that was impregnated consisted of $MgCl_2$—KCl with a molar ratio of 4:1.

EXAMPLE 3

Figure 6:
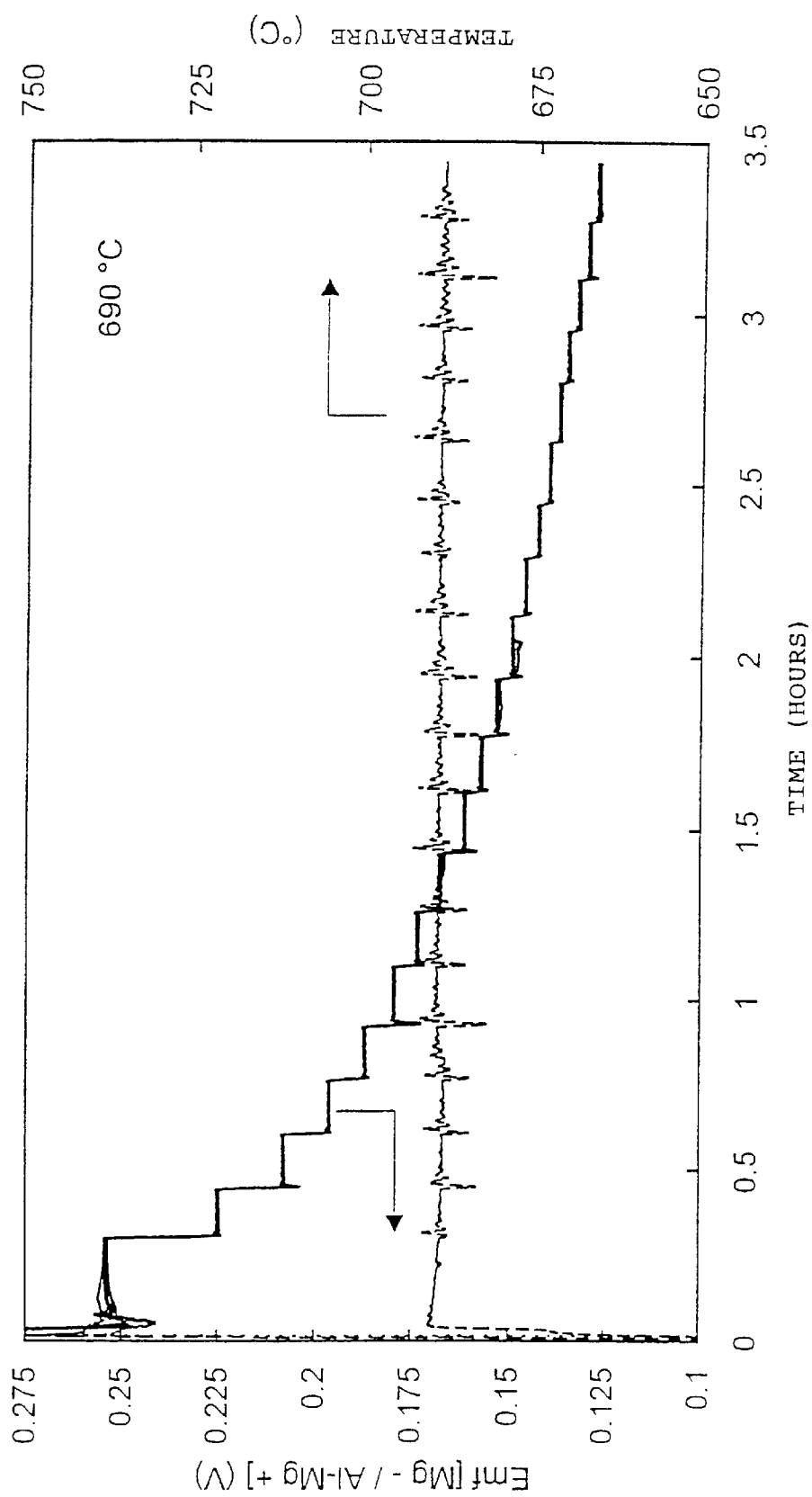
FIG. 6 gives the results of the measurement of the magnesium concentration in an aluminium melt in an induction furnace under air as a function of the measuring time whereby magnesium is added to the melt at regular time intervals.

Seven sensors according to this invention were used to measure the magnesium concentration in an aluminium-magnesium melt in an induction furnace under air. At regular times magnesium was added ti the melt. FIG. 6 gives an overview of the EMF behavior for all sensors at a temperature of 690° C. The experiment lasted for 3½ hours. Table 1 illustrates the reproducibility of the sensors: column 1 gives the magnesium concentration as analyzed with the spectrometer, while in column 2 tot 8 the EMF of the individual sensors is given, further column 9 and 10 contain the average value respectively the standard deviation for the seven sensors.

EXAMPLE 4

Figure 7:
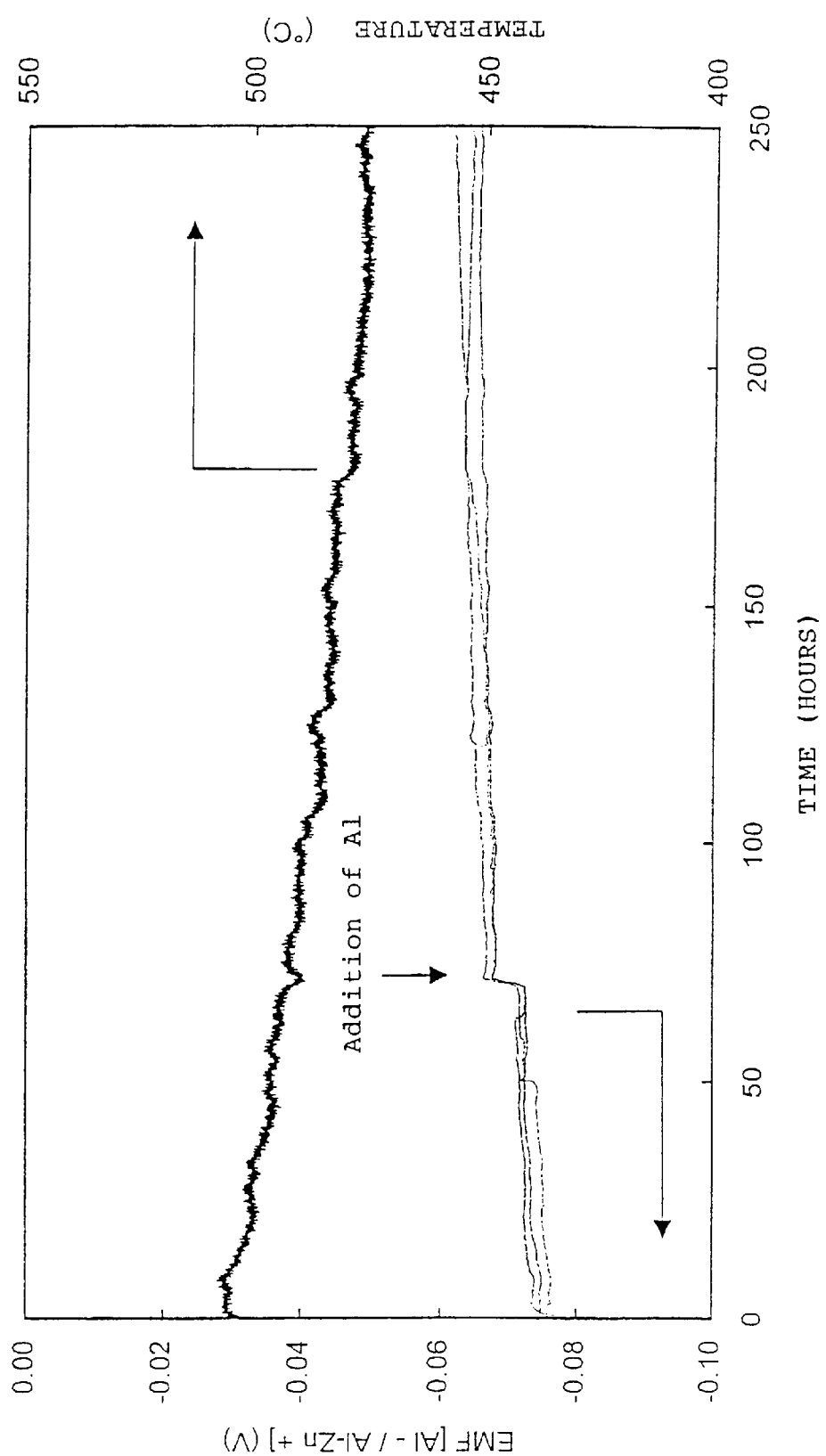
FIG. 7 gives the results of the measurements of the aluminium concentration in an aluminium-zinc alloy for galvanisation as function of the time and whereby aluminium is added to the melt.

The sensor according to this invention can be used to continuously and on-line measuring of aluminum in zinc, e.g. for the galvanization process. The sensor from example 1 can be used with the following essential adaptations:

- the halide contains aluminium, preferably aluminium chloride,
- the reference electrode contains aluminium, preferably pure aluminium metal, and
- the electric wire for the reference and measuring electrodess is inert to Zn—Al and to the halide and is preferably made of Ta. FIG. 7 gives a measurement with three sensors according to this invention in a zinc melt containing 0.2 wt % Al. The porous support was MgO with the same specifications as in example 2, the halide $AlCl_3$—NaCl (60–40 mol %), the reference was pure aluminium and the electric wires for the measuring and reference electrode were made from Ta. The temperature of the melt was between 470° C. and 510° C. These sensors also have a short reaction time upon immersion in the molten metal. Moreover, these sensors have a very long lifetime (longer than 1 week), which is very important in galvanization where one users the same bath during long time. Further, the reproducibility (about 1 mV) and the stability of the sensors are clear. An advantage of the sensors according to this invention is also that they can be introduced in (strongly) agitated melts.

What is claimed is:

1. An electrochemical sensor to measure the activity of a metallic component in a melt comprising:
   a) a measuring electrode comprising the melt;
   b) a reference electrode comprising
      i) the metallic component whose activity is to be measured,
      ii) an external connection comprising an electrically conducting wire held in an electrically isolating material which is substantially chemically inert to the melt and the reference electrode, and has a gas tight seal above the surface of the melt, and
      iii) a high-temperature-cement,
      wherein the reference electrode is sealed from the air by the melt, the high temperature-cement, the gas tight sealing of the external connection above the melt, and by melting the reference electrode inside the porous support; and
   c) a liquid ion-conducting halide that separates the measuring electrode and the reference electrode, wherein the liquid ion-conducting halide comprises the metallic component to be measured; and
   d) a non-conducting porous support that immobilizes the liquid ion-conducting halide, wherein said porous support is fabricated from a material that is substantially chemically inert to the melt, the halide, and the reference electrode.

2. The electrochemical sensor of claim 1, wherein the melt is an aluminum alloy.

3. The electrochemical sensor of claim 2, wherein the metallic component is Mg.

4. The electrochemical sensor of claim 1, wherein the melt is a zinc alloy.

5. The electrochemical sensor of claim 4, wherein the metallic component is Al.

6. The electrochemical sensor of claim 1, wherein the ion-conducting halide comprises chloride, fluoride, bromide, or combinations thereof.

7. The electrochemical sensor of claim 1, wherein the porous support is made from MgO.

8. The electrochemical sensor of claim 7, wherein the MgO powder used to fabricate the porous support has a purity of at least 99.5%.

9. The electrochemical sensor of claim 1, wherein the porous support has a porosity between 20 and 50%.

10. The electrochemical sensor of claim 9 wherein the porous support has a porosity between 30 and 40%.

11. The electrochemical sensor of claim 1, wherein the porous support has an average pore size between 0.5 and 5 $\mu$m.

12. The electrochemical sensor of claim 1, wherein the porous support is held in a holder of material which is substantially insoluble in the melt.

13. The electrochemical sensor of claim 12, wherein the holder comprises lips which can be used to hold the porous support.

14. The electrochemical sensor of claim 13, wherein the holder further comprises slits.

15. The electrochemical sensor of claim 12, wherein said holder is made of a non-conducting material.

16. The electrochemical sensor of claim 15, wherein said non-conducting material is alumina.

17. The electrochemical sensor of claim 12, wherein the holder is made from a functional conducting material, so that said holder serves as measuring electrode for the electrochemical cell.

18. The electrochemical sensor of claim 12, wherein the holder further comprises a thermocouple.

19. The electrochemical sensor of claim 12, wherein the porous support is obtained by compacting and subsequent sintering of MgO powder with a grain size distribution of at least 200 mesh.

20. The electrochemical sensor of claim 12, wherein the porous support is obtained by compacting and subsequent sintering of MgO powder, wherein the largest diameter of the MgO powder is 74 microns.

21. The electrochemical sensor of claim 1, wherein the porous support is protected by a cap made from a material that melts at a temperature that is equal to that of the melt.

22. Method for the production of an electrochemical sensor to measure the activity of a metallic component in a melt of a metal or alloy, comprising the melt as the measuring electrode, a reference electrode containing the metallic component to be measured, separated from each other by a liquid ion-conducting halide comprising the metallic component to be measured and immobilised in a non-conducting porous support fabricated from a material, substantially inert to the melt, the halide and the reference electrode material, and whereby the reference electrode further comprises an external connection consisting of an electrically conducting wire hold in an electric isolated protection being chemically substantially inert to the melt and the reference electrode material, characterised in that the method comprises the following successively executed steps:

sealing of the porous support containing the reference electrode material and the external connection, by means of a high temperature cement, immobilizing the halide into the porous support at a temperature higher than the melt temperature of the reference material, or melting the reference electrode material inside the electrochemical sensor followed by immobilizing the halide into the porous support at a temperature lower than the melt temperature of the reference electrode material, by which in both cases the reference electrode material is introduced by melting the reference electrode material inside the electrochemical sensor, sealing of the external connection of the reference electrode by a gas tight paste above the melt, and in-situ completion of the sealing of the sensor by total immersion in the melt of that part of the sensors containing the porous support.

23. A method of producing an electrochemical sensor to measure the activity of a metallic component in a melt comprising:

a measuring electrode comprising tie melt;

a reference electrode comprising
i) the metallic component whose activity is to be measured,
ii) an external connection comprising an electrically conducting wire held in an electrically isolating material which is substantially chemically inert to the melt and the reference electrode, and has a gas tight seal above the surface of the melt, and
iii) a high-temperature-cement,
wherein the reference electrode is sealed from the air by the melt, the high temperature-cement, the gas tight sealing of the external connection above the melt, and by melting the reference electrode inside the porous support; and a liquid ion-conducting halide that separates the measuring electrode and the reference electrode, wherein the liquid ion-conducting halide comprises the metallic component to be measured; and a non-conducting porous support that immobilizes the liquid ion-conducting halide, wherein said porous support is fabricated from a material that is substantially chemically inert to the melt, the halide, and the reference electrode, wherein the method comprises the steps of:
a) sealing the porous support containing the reference electrode material and the external connection, by means of a high temperature cement;
b) immobilizing the halide into the porous support at a temperature higher than the melting temperature of the reference material, or melting the reference electrode material inside the electrochemical sensor followed by immobilizing the halide into the porous support at a temperature lower than the melting temperature of the reference electrode material by which in both cases the reference electrode material is introduced by melting the reference electrode material inside the electrochemical sensor;
c) sealing the external connection of the reference electrode by a gas tight paste above the melt; and
d) totally immersing in the melt that part of the sensor containing the porous support, thereby completing, in-situ the sealing of the sensor.

* * * * *